(12) United States Patent
Zhou et al.

(10) Patent No.: US 10,888,615 B2
(45) Date of Patent: Jan. 12, 2021

(54) NEUTRALIZING HUMAN MONOCLONAL ANTIBODY 8D6 AGAINST HCV INFECTION

(71) Applicant: SUZHOU GALAXY BIOPHARMA, CO., LTD., Jiangsu (CN)

(72) Inventors: Honglin Zhou, Jiangsu (CN); Jie Liu, Jiangsu (CN); Xin Dong, Jiangsu (CN); Bing Sun, Shanghai (CN); Jiangjun Wang, Shanghai (CN); Zhiyang Ling, Shanghai (CN); Chunyan Yi, Shanghai (CN); Chao Bian, Shanghai (CN)

(73) Assignee: SUZHOU GALAXY BIOPHARMA, CO., LTD., Jiangsu (CN)

( * ) Notice: Subject to any disclaimer, the term of this patent is extended or adjusted under 35 U.S.C. 154(b) by 0 days.

(21) Appl. No.: 16/303,336

(22) PCT Filed: Apr. 21, 2017

(86) PCT No.: PCT/CN2017/081533
§ 371 (c)(1),
(2) Date: Nov. 20, 2018

(87) PCT Pub. No.: WO2017/206621
PCT Pub. Date: Dec. 7, 2017

(65) Prior Publication Data
US 2019/0298830 A1 Oct. 3, 2019

(30) Foreign Application Priority Data
Jun. 1, 2016 (CN) .......................... 2016 1 0382304

(51) Int. Cl.
| | |
|---|---|
| *A61K 39/42* | (2006.01) |
| *C07K 16/10* | (2006.01) |
| *A61P 31/14* | (2006.01) |
| *C12N 15/63* | (2006.01) |
| *G01N 33/569* | (2006.01) |
| *G01N 33/577* | (2006.01) |

(52) U.S. Cl.
CPC .............. *A61K 39/42* (2013.01); *A61P 31/14* (2018.01); *C07K 16/109* (2013.01); *C12N 15/63* (2013.01); *G01N 33/56983* (2013.01); *G01N 33/577* (2013.01); *C07K 2317/21* (2013.01); *C07K 2317/33* (2013.01); *C07K 2317/76* (2013.01); *G01N 2333/186* (2013.01)

(58) Field of Classification Search
None
See application file for complete search history.

(56) References Cited

FOREIGN PATENT DOCUMENTS

| | | |
|---|---|---|
| CN | 103642792 A | 3/2014 |
| CN | 105254756 A | 1/2016 |
| CN | 105330730 A | 2/2016 |
| WO | 02/08292 A2 | 1/2002 |
| WO | 2008/108918 A1 | 9/2008 |
| WO | 2010/039154 A1 | 4/2010 |
| WO | 2013/033319 A2 | 3/2013 |

OTHER PUBLICATIONS

Racanelli et al. (PLoS One, 2011, vol. 6 p. 1-11).*
International Search Report issued to International Application No. PCT/CN2017/081533, dated Jul. 12, 2017.
Written Opinion of the International Searching Authority for International Application No. PCT/CN2017/081533, dated Jul. 12, 2017.

* cited by examiner

*Primary Examiner* — Agnieszka Boesen
(74) *Attorney, Agent, or Firm* — Hoffmann & Baron, LLP

(57) ABSTRACT

Provided herein is a human monoclonal antibody 8D6 against hepatitis C virus (HCV) infection. The antibody binds to the E2 subunit of HCV capsid protein, and can prevent HCV from infecting susceptible host cells. By using the antibody variable region gene or the complementary determining region (CDR) gene, different forms of genetic engineering antibodies have been transformed and produced in any expression system of the prokaryotic and eukaryotic cells as therapeutics to prevent or treat HCV infection.

15 Claims, 4 Drawing Sheets

Specification includes a Sequence Listing.

SEQUENCE LISTING

```
<160> NUMBER OF SEQ ID NOS: 16

<210> SEQ ID NO 1
<211> LENGTH: 379
<212> TYPE: DNA
<213> ORGANISM: Homo sapiens

<400> SEQUENCE: 1
gaggtgcagc tggtgcagtc tgggtctgag ttgaagaagc ctggggcctc actgaagctc    60
tcctgcaagg cttctggata cacctacatt accccctgcca tgaactgggt gcgacaggcc   120
cctggacatg ggcttgagtg gatgggagga atcaacacca cactgggaa cccaacctat    180 gcccagggct tcgcaggacg gtttgtcttc tcctgggaca cctctgtcag cacggcatat   240
ctgcatatca gcagcctaaa gactgaggac actgccgtct attactgtgc ggacacccga   300
atcttttctt gtcggcgtgg aacgtgctat ggtggtttcg atgtctgggg ccaagggaca   360
atggtcaccg tctcttcag                                                379

<210> SEQ ID NO 2
<211> LENGTH: 126
<212> TYPE: PRT
<213> ORGANISM: Homo sapiens

<400> SEQUENCE: 2

Glu Val Gln Leu Val Gln Ser Gly Ser Glu Leu Lys Lys Pro Gly Ala
1               5                   10                  15

Ser Leu Lys Leu Ser Cys Lys Ala Ser Gly Tyr Thr Tyr Ile Thr Pro
            20                  25                  30

Ala Met Asn Trp Val Arg Gln Ala Pro Gly His Gly Leu Glu Trp Met
        35                  40                  45

Gly Gly Ile Asn Thr Asn Thr Gly Asn Pro Thr Tyr Ala Gln Gly Phe
    50                  55                  60

Ala Gly Arg Phe Val Phe Ser Trp Asp Thr Ser Val Ser Thr Ala Tyr
65                  70                  75                  80

Leu His Ile Ser Ser Leu Lys Thr Glu Asp Thr Ala Val Tyr Tyr Cys
                85                  90                  95
```

```
Ala Asp Thr Arg Ile Phe Ser Cys Arg Arg Gly Thr Cys Tyr Gly Gly
            100                 105                 110

Phe Asp Val Trp Gly Gln Gly Thr Met Val Thr Val Ser Ser
        115                 120                 125

<210> SEQ ID NO 3
<211> LENGTH: 322
<212> TYPE: DNA
<213> ORGANISM: Homo sapiens

<400> SEQUENCE: 3
gacatccaga tgacccagtc tccatcctcc ctgtctgcat ctgtaggaga cagaatcacc    60
atcacttgcc gggcaagtca gagcattagc aactttttaa attggtttca gcatagaccg   120
gggaaagccc ctaaactcct gatctatggt gcaaccattt gcaaagtggg gtcccatca   180 aggttcagtg gcagtggatc tgggacagat ttcactctca ccatcagcag tctgcaacct   240
gaagattttg caacttacta ctgtcaacag agtgacagta gtacctacat ctttggccag   300
gggaccaagg tggaaatcaa ac                                            322

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ser Ile Ser Asn Phe
            20                  25                  30

Leu Asn Trp Phe Gln His Arg Pro Gly Lys Ala Pro Lys Leu Leu Ile
        35                  40                  45

Tyr Gly Ala Thr Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Ser Thr Tyr
                85                  90                  95

Ile Phe Gly Gln Gly Thr Lys Val Glu Ile Lys
            100                 105

<210> SEQ ID NO 5
<211> LENGTH: 15
<212> TYPE: DNA
<213> ORGANISM: Homo sapiens

<400> SEQUENCE: 5
acccctgcca tgaac                                                    15

<210> SEQ ID NO 6
<211> LENGTH: 51
<212> TYPE: DNA
<213> ORGANISM: Homo sapiens

<400> SEQUENCE: 6
ggaatcaaca ccaacactgg gaacccaacc tatgcccagg gcttcgcagg a            51

<210> SEQ ID NO 7
<211> LENGTH: 57
<212> TYPE: DNA
```

<213> ORGANISM: Homo sapiens

<400> SEQUENCE: 7
gcggacaccc gaatctttc ttgtcggcgt ggaacgtgct atggtggttt cgatgtc          57

<210> SEQ ID NO 8
<211> LENGTH: 5
<212> TYPE: PRT
<213> ORGANISM: Homo sapiens

<400> SEQUENCE: 8

Thr Pro Ala Met Asn
1               5

<210> SEQ ID NO 9
<211> LENGTH: 17
<212> TYPE: PRT
<213> ORGANISM: Homo sapiens

<400> SEQUENCE: 9

Gly Ile Asn Thr Asn Thr Gly Asn Pro Thr Tyr Ala Gln Gly Phe Ala
1               5                   10                  15

Gly

<210> SEQ ID NO 10
<211> LENGTH: 19
<212> TYPE: PRT
<213> ORGANISM: Homo sapiens

<400> SEQUENCE: 10

Ala Asp Thr Arg Ile Phe Ser Cys Arg Arg Gly Thr Cys Tyr Gly Gly
1               5                   10                  15

Phe Asp Val

<210> SEQ ID NO 11
<211> LENGTH: 33
<212> TYPE: DNA
<213> ORGANISM: Homo sapiens

<400> SEQUENCE: 11
cgggcaagtc agagcattag caacttttta aat                                  33

<210> SEQ ID NO 12
<211> LENGTH: 21
<212> TYPE: DNA
<213> ORGANISM: Homo sapiens

<400> SEQUENCE: 12
ggtgcaacca ttttgcaaag t                                               21

<210> SEQ ID NO 13
<211> LENGTH: 27
<212> TYPE: DNA
<213> ORGANISM: Homo sapiens

<400> SEQUENCE: 13
caacagagtg acagtagtac ctacatc                                         27

<210> SEQ ID NO 14
<211> LENGTH: 11
<212> TYPE: PRT
<213> ORGANISM: Homo sapiens

```
<400> SEQUENCE: 14

Arg Ala Ser Gln Ser Ile Ser Asn Phe Leu Asn
1               5                   10

<210> SEQ ID NO 15
<211> LENGTH: 7
<212> TYPE: PRT
<213> ORGANISM: Homo sapiens

<400> SEQUENCE: 15

Gly Ala Thr Ile Leu Gln Ser
1               5

<210> SEQ ID NO 16
<211> LENGTH: 9
<212> TYPE: PRT
<213> ORGANISM: Homo sapiens

<400> SEQUENCE: 16

Gln Gln Ser Asp Ser Ser Thr Tyr Ile
1               5
```

NEUTRALIZING HUMAN MONOCLONAL ANTIBODY 8D6 AGAINST HCV INFECTION

CROSS-REFERENCE TO RELATED APPLICATIONS

The present application is the National Stage of International Application No. PCT/CN2017/081533, filed Apr. 21, 2017, which claims the benefit of Chinese Application No. CN 201610382304.8, filed Jun. 1, 2016, the entire contents of which are incorporated by reference herein

INCORPORATION BY REFERENCE

The specification is amended to direct entry of the Sequence Listing in the ASCII text file having i) the name HCV_SEQ_v6-20190613; ii) a date of creation of Jun. 13, 2019; and iii) a size of 6 kilobytes into the application. The material in that ASCII text file having i) the name HCV_SEQ_v6-20190613; ii) a date of creation of Jun. 13, 2019; and iii) a size of 6 kilobytes is incorporated by reference herein.

TECHNICAL FIELD

This invention relates to the fields of biotechnology and immunology; specifically, the invention relates to a human monoclonal antibody 8D6 against HCV infection. Compositions and methods are provided relating to human anti-HCV E2 monoclonal antibody. The antibody of the invention binds to a conserved region of the HCV E2 protein, and neutralizes HCV infection across multiple HCV genotypes. Embodiments of the invention include isolated antibodies and derivatives and fragments thereof, pharmaceutical formulations comprising one or more of the anti-HCV monoclonal antibodies; and cell lines that produce these monoclonal antibodies.

BACKGROUND

Hepatitis C caused by hepatitis C virus (HCV), generally spreads through blood and body fluids, and it is one of the major causes of various liver diseases. According to world health organization (WHO) statistics, there are about 150 million people worldwide suffering from chronic hepatitis C at present, and facing the risk of death as a result of liver failure or liver cancer. Every year, there are 300-400 million people are newly infected by HCV, and more than 350,000 people died of HCV-related liver diseases. The 2009 international liver disease summit data show that China, as a hepatitis C epidemic area, currently has about 40 million HCV patients. The probability of patients with acute HCV infection change into chronic hepatitis C is as high as 80%, which shows a clear trend of chronicity. End-stage liver disease caused by HCV is a leading indication of liver transplantation. However, reinfection with HCV occurs universally, and allograft failure due to reinfection is the most common cause of re-transplantation and death among HCV-infected liver transplant recipients. Over one third of recipients develop liver cirrhosis and need re-transplantation by the fifth postoperative year. Combined treatment with (pegylated) interferon and ribavirin has poor tolerability and efficacy in liver transplant recipients, with only approximately 30% sustained virological clearance occurring in treated patients. The incidence of HCV has increased 9 times in a decade in China. A safe, effective and inexpensive prevention and treatment of HCV is in urgent need around world.

HCV belongs to the Flaviviridae family (Flaviviridae) hepatitis c virus genera. HCV is spherical, about 60 nm in diameter (36-40 nm in liver cells, 36-62 nm in the blood), the internal is a single RNA chain, the nucleocapsid is wrapped with lipid envelope which has spikes. The full length of HCV RNA genome single strands is about 9.6 KB, contains 5'- and 3'-end (non-translated region, UTR) and an open reading frame (ORF), encoding a 3000 amino acid polymer precursor protein, which can translate and shear for 11 viral proteins. N-end of HCV RNA encodes five structural proteins containing Core (F), E1, E2 and P7, while C-terminal coded six nonstructural proteins of NS2, NS3, NS4A, NS4B, NS5A and NS5B. Among them, the core protein is the most basic composition of virus capsid; E1/E2 is high-glycosylated virus envelope protein; P7 is ion channel protein which mediates virus particles assembly and release; NS2, NS4B, NS5A, NS5B are involved in virus replication; NS3-4 is involved in shearing virus polymer precursor protein.

Currently there is no vaccine for preventing HCV infection, and the combination therapy of polyethylene glycol interferon-α with ribavirin is the standard treatment for chronic hepatitis C. However, based on the infected virus genotype and other factors, only 50-80% of patients can produce sustained viral response (SVR), while other patients' condition cannot get controlled by this treatment. In May 2011, the FDA approved two anti-HCV drugs, Victrelis (-1-boceprevir) and Incivek (telaprevir). These two drugs belong to protease inhibitors, which can prevent hepatitis C virus replication. The treatment of these two drugs can effectively reduce the RNA load of HCV, but also face the problems including drug resistance, side effects, high prices and other issues, which have restricted its clinical use.

A model for HCV antibody therapy is available in liver transplantation for hepatitis B (HBV). While nucleotide and nucleoside analogs are well tolerated and effective for suppression of HBV, hepatitis B immunoglobulin (HBIg) is required and is a standard of treatment for prevention of post-liver transplant HBV infection. HBIg has moved HBV infected patients from the ranks of the not transplantable to ideal candidates for liver transplantation. Thus, an effective hepatitis C immunoglobulin is a potential solution for preventing post-liver transplant HCV infection, even if more efficacious and well tolerated oral antivirals are developed.

Antibody for treating virus infections have been well-documented, cases of antiserum for treatment of SARS and H5N1 in severe viral infection have proved that antibody play an important role in the treatment of viral infections. Anti-HCV monoclonal antibody with neutralizing activity has the following potential advantages: on one hand, it can block the binding between the virus and target cell; on the other hand, it acts together with the complement system, T cells, NK cells and other immune effector cells to eliminate viral-infected cells. In 1986, the first murine mAb muromonab-CD3 (murmonabCD3, clone OKT3), which treats rejection of organ transplant, was approved by United States FDA, but there are limitations of its application, which caused by its human-anti-mouse antibody (HAMA) reaction in the human body. In this case 8D6 is a human antibody which minimizes the risk of HAMA in clinic treatment.

E2 in HCV envelope protein plays an essential role in the process of virus invasion, it is the major binding region for HCV viral particle on the cell surface. In addition, E2 is also the major target for eliciting the immune response. E2 N-terminal contains two hypervariable regions (HVR), HVR1 and HVR2 respectively, which are on the surface. Studies have shown that HCV chronic infection and viral escape are closely related to these two regions. At present, the widely recognized broad-spectrum neutralizing epitope is AR3 epitope, which contains three discontinuous amino acids (396-424, 436-447 and 523-540).

In summary, the development of fully human monoclonal antibody 8D6 targeting the E2 protein in HCV has significant potential for the future prevention and treatment of HCV.

SUMMARY OF THE INVENTION

The invention aims to provide an anti-HCV monoclonal neutralizing antibody. Compositions and methods are provided relating to human anti-HCV E2 monoclonal antibody 8D6. The antibody of the invention binds to a conformational epitope in a conserved and essential region of HCV E2 protein, and neutralizes HCV infections across multiple HCV genotypes. Embodiments of the invention include the isolated antibodies and derivatives and fragments thereof, pharmaceutical formulations comprising one or more of the human anti-HCV monoclonal antibodies; and cell lines that produce these monoclonal antibodies. Also provided are CDR amino acid sequences that confer the binding specificity of these monoclonal antibodies. These sequences and the cognate epitopes to which the monoclonal antibodies of the invention bind can be used to identify other antibodies that specifically bind and neutralize HCV; and immunotherapeutic methods for prevention of disease associated with HCV virus, including but without limitation to the neutralization of virus in association with liver transplantation. Therapies of interest include combination therapies with anti-HCV therapeutics such as monoclonal antibodies that specifically bind a different epitope than the antibodies of the invention, small molecule antivirals, interferon, and the like.

The compositions of antigens are provided, which comprise all or a portion of an HCV E2 protein in which specific highly immune-dominant residues are masked, so as to generate an immune response to residues that are less immune-dominant, but which are essential for virus function and therefore less likely to be altered during virus escape mutation and selection. Such polypeptides are typically at least about 50 amino acids of contiguous E2 sequence, at least about 100 amino acids, at least about 200 amino acids, up to substantially all of the E2 protein. These antigens found use in screening assays can be used as an anti-HCV vaccine composition to stimulate generation of monoclonal antibodies.

In one aspect, the present invention provide an isolated binding molecule, including CDR1 heavy chain set forth in SEQ ID NO:8, CDR2 heavy chain set forth in SEQ ID NO:9, CDR3 heavy chain set forth in SEQ ID NO:10.

In one aspect, the present invention provide an isolated binding molecule, including CDR1 light chain set forth in SEQ ID NO:14, CDR2 light chain set forth in SEQ ID NO:15, CDR3 light chain set forth in SEQ ID NO:16.

In one aspect, the present invention provide an isolated binding molecule, including CDR1 heavy chain set forth in SEQ ID NO: 8, CDR2 heavy chain set forth in SEQ ID NO: 9, CDR3 heavy chain set forth in SEQ ID NO: 10, CDR1 light chain set forth in SEQ ID NO: 14, CDR2 light chain set forth in SEQ ID NO: 15, CDR3 light chain set forth in SEQ ID NO: 16.

In a preferred embodiment, the molecule set forth includes heavy chain variable region, which including the amino acid sequence set forth in SEQ ID NO: 2.

In a preferred embodiment, the molecule set forth includes light chain variable region, which including the amino acid sequence set forth in SEQ ID NO: 4.

In a preferred embodiment, the molecule set forth includes heavy chain variable region and light chain variable region, which including the amino acid sequences set forth in SEQ ID NO: 2 and SEQ ID NO: 4.

In a preferred embodiment, the binding molecules set forth are Fab, F(ab'), F(ab')$_2$, Fv, dAb, Fd, complementarity determining region (CDR) fragment, scFv, bivalent single-chain antibody, single-chain phage antibody, double specific double-chain antibody, triabody, four-chain antibody;

Preferably, the binding molecule set forth is human monoclonal antibody; more preferably, the binding molecule set forth contains IgH sequence and Igκ sequence in constant region.

More preferably, the heavy chain variable region and light chain variable region of the humanized monoclonal antibody contain the amino acid sequences set forth in SEQ ID NO: 2 and SEQ ID NO: 4, and the heavy chain constant region chooses the constant region in the following heavy chain types: IgG1, IgG2a, IgG2b, IgG3 and IgG4, while the light chain constant region chooses the constant region in the following light chain types: κ chain and λ chain.

Preferably, the heavy chain variable region and light chain variable region of the humanized monoclonal antibody contain the amino acid sequences set forth in SEQ ID NO: 2 and SEQ ID NO: 4, and the heavy chain constant region and light chain constant region contain the amino acid sequences set forth in Genebank No. ACK87036 and ACK87038 respectively.

In a preferred embodiment, any of the molecules can recognize and bind the epitope in HCV envelope protein.

In one aspect of the invention, the nucleic acid molecules encoding the binding molecules are provided.

In another aspect of the invention, the use of any of the preceding binding molecules in the preparation for the detection, treatment and/or prevention of hepatitis C virus infection is provided.

On the other hand, the invention provides an expression vector containing a DNA that encodes the binding molecule in front of any one of the binding molecules.

In another aspect of the invention, a host cell is provided that contains the expression vector.

On the other hand, the invention provides a composition comprising a binding molecule in front of any one, and a pharmaceutical acceptable carrier.

On the other hand, the invention provides a reagent kit for detecting hepatitis C virus, which comprises a binding molecule in front of any one of the binding molecules.

In a preferred embodiment, the kit also includes: antigen or antibody coated reagent, washing reagent, the second antibody, markers (such as horseradish peroxidase, alkaline phosphatase, glucose oxidase, β-D half 10 lactose glucoside enzyme, urease, and catalase or glucose amylase), and chromogenic agent enzyme substrate.

In one aspect of the invention, providing a suppression method of hepatitis C virus (preferably for a non-treatment), using either of the binding molecules to inhibit the hepatitis C virus.

In one aspect of the invention, providing a detection method of hepatitis C virus (preferably for a non-diagnostic method), using either of the binding molecules contact with samples to be measured, to achieve the existence and amount of hepatitis C virus by detecting the combination state of binding molecules and tested samples.

In a preferred embodiment, the hepatitis C virus is 1a subtype, 1b subtype, 2a subtype virus, 2b subtype, 3a subtype, 4a subtype, 5a subtype, 6a subtype, or 7a subtype.

In a preferred embodiment, the hepatitis C virus 1a subtype includes: H77 strain; or The hepatitis C virus 1b subtype includes: PR52B6M strain, PR79 strain, PR26C3M 20 strain, Con1 strain, HCR6 strain, PR52 strain, PR26 strain, PR79 strain, or The hepatitis C virus 2a subtype includes: D183 strain, JFH1 strain, PR63 strain; or The hepatitis C virus 2b subtype includes: J8 strain; or The hepatitis C virus 3a subtype includes: Patient 288 strain, S52 strain; or The hepatitis C virus 4a subtype includes: ED43 strain; or The hepatitis C virus 5a subtype includes: SA13 strain; or The hepatitis C virus 6a subtype includes: HK6a strain, 74 strain; or The hepatitis C virus 7a subtype includes: QC69 strain.

Other aspects of the invention are obvious to the technical personnel in the field because of the disclosure.

BRIEF DESCRIPTION OF THE DRAWINGS

The invention can be better understood by referring to the drawings in the embodiments of the present invention, in the attached drawing.

DETAILED DESCRIPTION OF THE INVENTION

Figure 1:
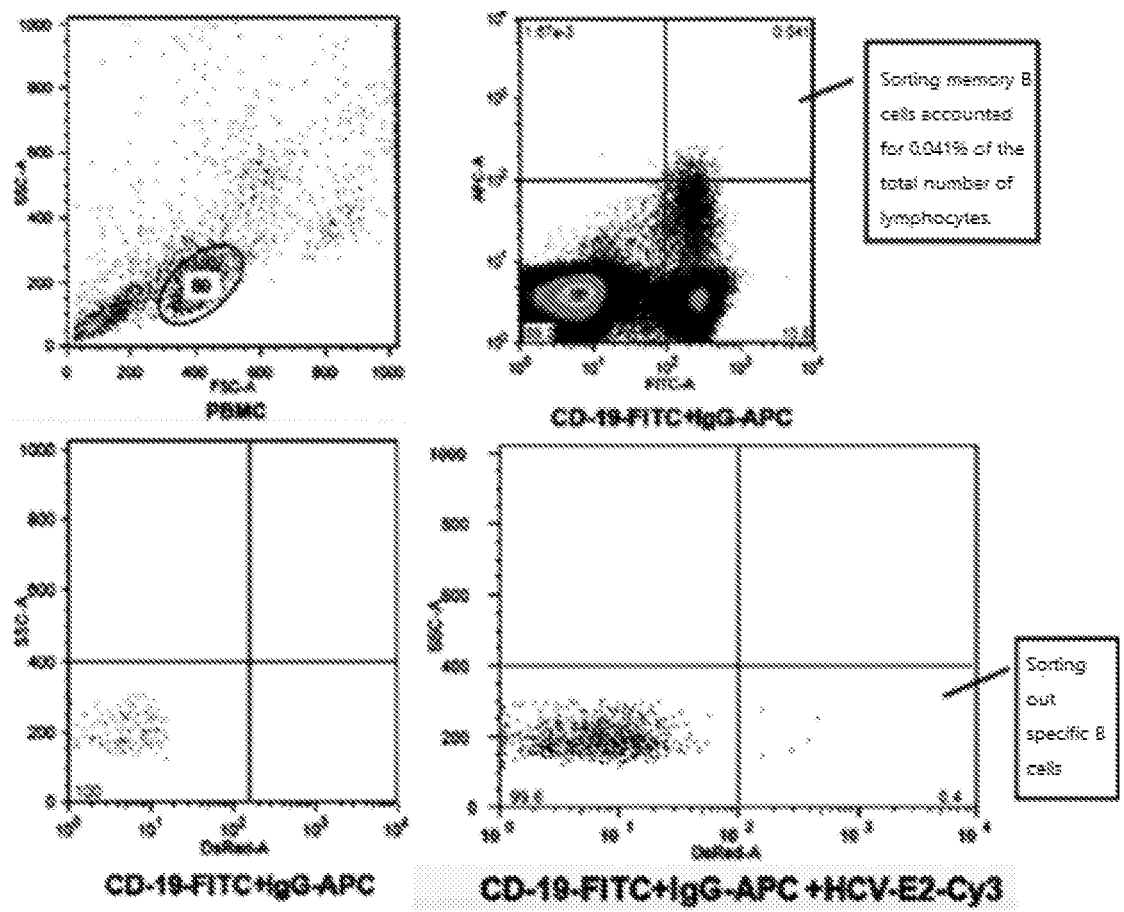
FIG. 1 Sorting of specific B cells by FACS

After widely and in-depth research, the present inventors achieve an anti-HCV neutralizing antibody containing a unique complementarity-determining region (CDR), preferably human monoclonal antibody (8D6), and this binding molecule has significant neutralization effect for hepatitis C virus. The invention is completed on this basis.

Binding Molecules

The present invention provides a binding molecule that can specifically binds to hepatitis C virus. The binding molecule of the present invention presents a neutralizing activity for hepatitis C virus The binding molecule of the invention can be a whole immunoglobulin molecule, an antigen binding fragment, including but not limited to Fab and F(ab'), F(ab') 2, Fv, dAB, Fd, complementarity-determining region (CDR) fragment, single chain antibody (scFv), bivalent single chain antibody, single strand phage antibody, double specific double-chain antibody, three-chain antibodies, antibody with four chains and (multi) peptide or its fragments contains at least sufficient to confer with hepatitis C virus specific antigen binding.

The binding molecule of the present invention may also bind specifically to one or more fragments of hepatitis C virus. For the treatment and/or prevention of HCV, the binding molecule can be specifically binds to the surface of the HCV and the protein. In a specific embodiment, the binding molecule of the present invention can bind specifically to HCV E2 molecules.

The invention also provides the medical application of the binding molecule in diagnosis, prevention and/or treatment of hepatitis C virus infection. The present invention provides a binding molecule that can neutralize HCV caused by HCV infection.

CDR region is a protein sequence of interest in immunology. In the embodiment of the invention, the binding molecules may include two or three, four or five or all six CDR regions revealed in this article. Preferably, the combination molecule of the present invention comprises at least two CDR that are disclosed herein.

On the other hand, the present invention comprises a functional variant of the binding molecule. If variants can competitively bind to HCV or protein fragments with the parental combining molecule, and then it is assumed that the molecular variant is a functional variant of the combination molecule. In other words, the functional variants are still capable of binding to hepatitis C virus E2 protein or fragments thereof. Functional variants, including but not limited to those with similar primary structure sequence, but contain in vitro or in vivo chemical and/or biological chemical modified derivatives found in the parental binding molecules. Such modifications include acetylation, acylation, nucleotides or nucleotide derivatives covalently attachment, lipid or lipid derivatives of covalent attachment, crosslinking, disulfide bond formation, glycosylation, hydroxylation, methylation, oxidation, pegylation, enzymatic hydrolysis process, phosphorylation, etc. In other words, modification in amino acids and/or nucleotide sequence of the parental binding molecules does not significantly affect or change the binding properties of the binding molecules encoding by the nucleotide sequence or containing the amino acid sequence, that is, the binding molecules can still recognize and bind to its target.

The functional variants may have conserved sequence modifications, including substitutions, additions and deletions of nucleotide and amino acid. These modifications can be imported by standard techniques known in the field, such as directed mutagenesis and random PCR mediated mutagenesis, and can include natural and non-natural nucleotides and amino acids.

Conservative substitution of amino acid, amino acid residues are replaced by another amino acid residue with similar structure or chemical properties. The family of amino acid residues with similar side chain has been defined in this field. The family includes amino acids with basic side chains (such as lysine, arginine and histidine), amino acids with acidic side chains (such as aspartic acid, glutamic acid), amino acids with no-charge polar side chains (for instance, asparagine, glutamine, serine, threonine, tyrosine, cysteine, tryptophan acid), amino acids with non-polar side chains (such as glycine, alanine, valine, leucine, isoleucine, proline, phenylalanine, methionine), amino acids with side branch chains (for example threonine, valine, isoleucine) and amino acids with aromatic side chains (e.g. tyrosine, phenylalanine, tryptophan). Other classification methods of amino acid residues are known to those of skill in the art. In addition, variants may be substituted with non-conservative amino acids, such as amino acids, which have different structure or chemical properties. Similar small variations may also include deletion or insertions of amino acids, or both. A computer program known in this field can be used to determine which amino acid residues can be replaced, inserted, or deleted without eliminating the immune activity.

In addition, the functional variants may include an amino acid group or a carboxyl terminal or the truncation at both ends. Compare to parental binding molecules of the invention, the functional variants have the same or different, higher or lower affinity, but still can bind to HCV or a fragment thereof. Preferably, the variable region includes, but not limited to, the amino acid sequence of the frame area, the high variable region or the CDR region. Usually, the light chain and heavy chain variable regions contain three high variable regions, including three CDR, and a more conserved region, the so-called framework region (FR). The hypervariable region contains amino acid residues from the CDR and from hypervariable amino acid residues. In the scope of the present invention, functional variants and the parental binding molecules with at least about 50% to about 99%, preferably at least about 60% to about 99%, more preferably at least about 70% to about 99%, even more preferably at least about 80% to about 99%, and most preferably at least about 90% to about 99%, especially at least approximately 95% to about 99%, and especially at least about 97% to about 99% homology in amino acid sequence. The computer algorithms known as Gap or Bestfit can be used for the best arrangement of amino acid sequences to compare with similarity or identify amino acid residues. Functional variants can be obtained by a known common molecular biological method to change the parental molecules or a part of it, and the method includes but not limits to, error prone PCR and oligonucleotide-directed mutagenesis, site-directed mutagenesis and heavy chain and/or light chain reorganization method. In one embodiment, the functional variants of the present invention have neutralizing activity to hepatitis C virus. The neutralizing activity compared with the parental binding molecules can be the same or higher or lower. Thereafter, when using the term (human) binding molecules, it also covers the functional variants of the (human) binding molecules.

As a preferred method of the present invention, the binding molecule is a monoclonal antibody that preferably comprises a human constant region (e.g., a humanized constant region IgH sequence and Igκ sequence). In this anti-HCV monoclonal antibody, the heavy chain variable region, light chain variable region, and complementarity determining regions (CDRs) in the variable region of heavy chain and light chain variable region, has a unique structure which is different from the existing technology.

The invention includes: a monoclonal antibody with corresponding amino acid sequence of the monoclonal antibody, and a monoclonal antibody with the variable region chain of the monoclonal antibody. The invention also includes is containing the light chain of the complementarity determining regions (CDRs) and any antibody of heavy chain, and any monoclonal antibody has more than 90% (preferably more than 95%) homology CDR regions to those of the monoclonal antibody in this invention.

Antigen binding characteristics of the antibody can be described by three specific regions located in the heavy chain and light chain variable region, known as complementarity determining regions (CDRs), which divides the variable region into 4 framework region (FR) which are relatively conservative, and not directly involved in binding reactions. These CDRs form a ring structure, through FR forming a β folding on the spatial structure to be closed to each other, CDR on the heavy chain and the corresponding CDR on the light chain constitute the antibody antigen binding site. Amino acid sequences of the same type of antibody can be compared to determine which amino acid constitutes the FR or CDR region.

The heavy chain and light chain sequences of the monoclonal antibody in the present invention can be determined by common methods.

It is verified that, the CDR regions of the anti-HCV monoclonal antibody 8D6 in the invention is new, and it is against a unique HCV E2 protein epitopes, and the technical conception is different from the existing anti-HCV antibody.

The monoclonal antibody of the invention is fully human, and the heavy chain, the light chain variable region and the constant region are all derived from human antibody. Therefore, it recognizes and neutralizes HCV with low immunogenicity and high safety as a therapeutic antibody.

In embodiments of the present invention, peripheral blood mononuclear cells (PBMC) are extracted from volunteers who are infected HCV recently, using CD19+/IgG+/HCV-E2 as specific markers, to obtain specific B cells recognizing HCV E2 protein by fluorescence activated cell sorting (FACS). Using single cell RT-PCR technique (Journal of Immunological Methods 329 (2008) 112-124), the antibody genes were obtained and humanized monoclonal antibody 8D6 is expressed in 293T cells. Neutralization experiment of envirus (HCVcc) showed that the 8D6 antibody has more than 90% inhibition rate at lower concentration (0.4 g/ml below) for some HCV envirus. Thus, 8D6 antibody has a strong affinity and neutralizing activity, which has the possibility for clinical prevention and treatment of HCV infection.

On the other hand, the present invention includes immune conjugates, which includes the at least a binding molecule and also contains at least a marker such as molecule of a detectable part/a substance. The invention also relates to a mixture of immune conjugates in the invention or at least a mixture of the immune conjugates in present invention and another molecule such as treatment agent or another binding molecule or immune conjugates. Immune conjugates of the invention can include more than one marker. These markers can be the same or different from each other, and can non-covalently bind/conjugate to binding molecules. These markers may also covalently bind/conjugate to binding molecules directly. Or, the markers can bind/conjugate to binding molecules with one or more binding molecules. The conjugation technology of the markers and binding molecules are known to those skilled in the art.

The marker of immune conjugates in the invention can be a therapeutic agent, but they also can be a detectable part/substance. Markers suitable for treatment and/or prevention may be toxins or its functional part, antibiotics, enzymes, other binding molecule with enhanced phagocytosis or immune stimulating effect. Immune conjugates containing detectable substance can be diagnostic used for such as evaluation if subject is already infected with hepatitis C virus or as a part of clinical trials program to monitor the incidence or development of hepatitis C virus, for example, to determine the efficacy of a specified treatment.

However, they can also be used for other detection and/or analysis and/or diagnostic purposes. Detectable part/substance includes but not limits to the enzyme, prothetic group, fluorescent materials, luminous materials, bioluminescence materials, radioactive materials, positron emission metal and non-radioactive paramagnetic metal ion. Markers used for labeling binding molecules, which is for detect and/or analysis and/or diagnostic purposes, is dependent on the use of a particular detection/analysis/diagnosis technology and/or methods, such as immunohistochemistry staining (tissue) samples, flow cytometry measurement technique, laser scanning cell measurement detection, immunofluorescence assay, enzyme-linked immunosorbent assay (ELISA), radio-immunoassay (RIA), bioassay (such as phagocytosis assay), western blotting, etc. detection/analysis/diagnostic techniques and/or methods as a suitable marker known in this area are familiar to those skilled in the art.

In addition, the human binding molecules or immune conjugates in the invention can also be attached to a solid phase, especially for in vitro immunoassay or purification of HCV E2 protein or a fragment thereof. The solid phase may be porous or non-porous, planar or non-planar. The binding molecules of the invention can be fused with a sequence of markers to facilitate purification. The sequence of marker includes but is not limits to six histidine marker, myc marker, or flag markers. Or, an antibody can conjugate with another antibody to form heterologous antibody conjugates (hetero-conjugates).

On the other hand, binding molecules of the invention can conjugate/attach with one or more antigen. Preferably, these antigens are recognized by the immune system with an object of binding molecule-immune conjugates. The antigens may be the same or different to each other. The method of attaching binding molecule to the antigen is known in this field, including but not limiting to the use of crosslinking agent. The binding molecules of the invention bind to HCV and attach an antigen, will trigger an attack for the T cells which is powerful to the conjugates, which eventually lead to the destruction of the HCV.

In addition to direct or indirect (e.g. through joint) conjugation to produce immune conjugates, the immune conjugates can be produced as a fusion protein containing binding molecules and suitable markers of the invention. Fusion protein can be produced by the methods known in the art, for example, expressing nucleic acid after construction to recombine and produce, and the nucleic acid molecule contains nucleotide sequence conforming to the reading frame coding and encoding suitable markers.

In another aspect of the invention provides nucleic acid molecules encode at least one binding molecules, the functional variant or immune conjugates. This nucleic acid molecule can be used as an intermediate for cloning, for example, used in affinity maturation as described above. In a preferred embodiment, the nucleic acid molecules are isolated or purified. The sequence of DNA molecules can be obtained by conventional techniques, or hybrid techniques.

Technical personnel in this field will be aware of the functional variants of these nucleic acid molecules is part of the invention. A functional variant is the nucleic acid sequence, which can direct translate with the standard genetic code to provide same amino acid sequence from parental DNA molecule translation.

Once the relevant sequences are obtained, we can use the method to get the relevant sequences in large quantities. This is usually cloned into the vector, and then transferred to the cell, then separate the relevant sequence from the proliferated host cell through the conventional method.

In addition, synthetic methods can be used to synthesize relevant sequences, especially when the fragment length is short. Usually, a number of small fragments are synthesized firstly, and then connect to get a long sequence of fragments.

At present, the DNA sequences of the binding molecules (or fragments thereof, or derivatives thereof, or derivatives thereof) can be obtained completely by chemical synthesis. The DNA sequence can then be introduced into the existing 10 kinds of DNA molecules (or the vectors) and the cells which are known in the field. In addition, the mutation is introduced into the sequence of the binding molecules in the present invention through chemical synthesis.

The invention also includes the appropriate DNA sequences set forth above and an appropriate promoters or vectors controlling sequences. These vectors can be used to transform the appropriate host cells to express proteins. Preferably, the vectors of the invention is for example plasmid expression vector containing virus promoter, and the expression vector insert into the anti-HCV monoclonal antibody heavy chain variable region (VH) and n IgH fusion sequence of constant region (from constant region of humanized IgH) and light chain variable region VL and human Igκ fusion sequence.

The host cell may be prokaryotic cells, such as a bacterial cell; or lower eukaryotic cells, such as yeast cells; or higher eukaryotic cells, such as mammalian cells. Representative examples are: bacterial cells such as *Escherichia coli, Aphanomyces* spp; *Salmonella typhimurium*; fungal cells such as yeast; plant cells; insect cells such as *Drosophila melanogaster* S2 or Sf9; animal cells such as CHO, COS7, NSO or Bowes melanoma cells. In particular, the host cell of the present invention is a eukaryotic host cell, especially mammalian cells, such as 293 cells.

Transforming host cells through recombinant DNA can be done by a conventional technology known in the field. When the host is prokaryotic cells such as *Escherichia coli*, absorption of DNA competent cells can be obtained in the exponential growth phase, the steps of $CaCl_2$) treatment methods are known in this field. Another method is to use $MgCl_2$. If necessary, electroporation can be used for transformation. When the host is eukaryotic cells, the following methods can be used for DNA transfection: calcium phosphate co-precipitation method, or conventional mechanical method such as microinjection, electroporation, liposome packaging etc.

The obtained converter can be cultured by the conventional method, and express the binding molecule of the invention. According to the host cells, culture medium can be selected from a variety of conventional culture. Host cells are cultured under the conditions which is suitable for the growth. When the host cell is grown to the appropriate cell density, the promoter is induced by suitable methods (e.g., temperature conversion or chemical induction), and then the cells will be cultured for a period.

The binding molecules of the present invention are preferably produced by mammalian cells, and the mammalian cells usually need to be incubated in a medium containing serum. The cells can be incubated in the serum-free medium after adapt to the serum-free culture.

If required, the recombinant protein can be isolated and purified by various methods based on its physical, chemical and other properties. These methods are well known to the technical staff in this field. Examples of these methods include, but not limited to: conventional renaturation, protein precipitation (salting out method), centrifugal, penetrate bacteria, ultrasonic treatment, ultracentrifugation, molecular sieve chromatography (gel filtration), adsorption chromatography, ion exchange chromatography, high performance liquid chromatography (HPLC) and other kinds of liquid phase chromatography and the combination of these method.

The binding molecules of the invention also can be produced in transgenic non-human mammals such as rabbits, goats, or cows, and are secreted, such as in the milk.

Pharmaceutical Composition

The binding molecules of the invention can be used to prepare an anti-HCV composition.

Based on the new discoveries of the invention, also a composition of anti-HCV or HCV infected disease is provided, including: an effective amount of the binding molecules in the invention; and a pharmaceutically acceptable carrier.

In this invention, the term "pharmaceutical acceptable" means that when the molecular body and composition are properly administered to animals or human, they will not produce adverse, allergic or other adverse reactions. The "pharmaceutical acceptable carrier" used in this invention shall be compatible with the binding molecule of the present invention, that is, to be able to mix rather than reducing the effect of the composition in the ordinary circumstances.

Some particular examples of pharmaceutical acceptable carrier and its composition are saccharides, such as lactose, glucose and sucrose; starch, such as corn starch and potato starch; cellulose and its derivatives, such as carboxymethyl cellulose fiber, ethyl cellulose and sodium carboxymethyl cellulose; tragacanth powder; malt; gelatin; talc; solid lubricants, such as stearic acid and magnesium stearate; calcium sulfate; vegetable oils, such as peanut oil, cottonseed oil, sesame oil, olive oil, corn oil and cocoa oil; polyols, such as propylene glycol, glycerol, sorbitol, mannitol and polyethylene glycol; alginic acid; emulsifier, such as Tween; wetting agent, such as sodium lauryl sulfate; colorant; flavoring agent; compression agent, stabilizer; antioxidant; preservatives; pyrogen-free water; isotonic salt solution and phosphate buffer solution.

The composition of the invention can be made into various dosage forms based on the requirements, and physician can determine the beneficial dosage for the patient according to the factors such as the type of the patient, the age, the body weight and the general condition of the disease, and the administration routes. The administration routes include injection or other treatment methods.

The binding molecules of the present invention can be separated or to be used in the form of separation. In addition, the invention can be used alone or in a combination containing at least one of the binding molecules (or a variant or fragment thereof) in the present invention. In other words, the binding molecule may be used in the combination, such as a pharmaceutical composition comprising binding molecules with two or more of the present invention, a variant or fragment thereof. For example, binding molecules with different but complementary activity can be combined in a treatment plan to achieve the prevention, treatment or diagnosis, but is or can combined the binding molecules with the same activity with a treatment plan in order to achieve prevention, therapeutic or diagnostic role. Optionally, the mixture comprises at least one other therapeutic agent. Preferably, the therapeutic agent, such as ribavirin, can be used for the prevention and/or treatment of HCV infection.

The pharmaceutical composition may comprise two or more binding molecules with neutralizing activity for hepatitis C virus. In one embodiment, when the combination is applied, the binding molecules present a synergistic neutralization activity. In other words, the composition comprises at least two binding molecules with neutralizing activity, and binding molecules play a synergistic role in neutralizing the hepatitis C virus. In this invention, the term "synergistic" means that the combination effect of the binding molecules in combination application is higher than that of the adduction effect in single application. The synergistic effect of the binding molecules can be combined with different structures on the same or different fragments of the hepatitis C virus. The calculation of synergistic effect is based on the combination of exponential calculation. The concept of composite index (CI) has been described by Chou and Talalay (Ting-Chao Chou. Quantitative analysis of dose-effect relationships: the combined effects of multiple drugs or enzyme. Advances in Enzyme Regulation (1984); Volume 22: Pages 27-55).

The binding molecules of the present invention or pharmaceutical composition can be detected in a suitable animal model system before applied in human. This kind of animal model includes but not limited to, mouse, ferret and monkeys. Anti-HCV small molecule compounds also can be synergistic.

The dosage regimen can be adjusted to provide the best response (such as therapeutic response). The appropriate dose range can be, for example, 0.01-100 mg/kg body weight, preferably 0.1-15 mg/kg body weight. In addition, for example, a bolus can be given, a number of separated doses can be given with the time goes, or increase or reduce dose according to the urgency of the treatment situation.

The molecules and compositions of the present invention are preferably sterile. The sterilization methods for these molecules and compositions are well known in the field. Other molecules for the diagnosis, prevention and/or treatment can be administered in a similar route as that of the binding molecules in the present invention. If other molecules are given separately, it can be considered to be given before, at the same time, or after one or more human binding molecules or combination of the invention. The precise dosing regimen for human patients is usually selected during clinical trials.

Detection Reagent and Kit

The binding molecules of the present invention can be used to prepare reagent and kit for detecting HCV.

As used herein, the term "sample to be measured" covers a wide range of sample types, including blood and other body fluid samples from biological source, and solid tissue samples such as biopsy samples or tissue cultures, or cells or its offspring derived from them. The term also includes samples treated with other methods after obtaining, such as treatment with reagents, dissolution, or enrichment of some components such as proteins or polynucleotides. The term covers various clinical samples of any species, including the cultivation of cells and cell culture supernatants and cell lysis products On the basis of the binding molecule, a convenient, quick and accurate kit can be prepared to detect HCV. Therefore, the present invention provides a detection kit for detecting the presence of HCV in a sample, comprising a binding molecule of anti-HCV in the present invention. After obtaining the binding molecule provided by the present invention, the detection kit can be conveniently prepared for specific detection of HCV. As a detection method of the present invention, the binding molecules of the present invention can detect the antigen coated on a solid phase by an indirect ELISA method. As a preferred method of the invention, the binding molecule is an antibody, which can be detected by the double antibody sandwich method. The steps of double antibody sandwich method are fix the primary antibody (such as the monoclonal antibody of the present invention)

on a carrier, which reacts with the antigen, and then reacts with the secondary antibody (the secondary antibody contains a detectable signal, or can combine to the substance carrying detectable signal) after washing, finally the signal can be detected by chemiluminescence or enzyme linked coloring reaction. The double antibody sandwich method is especially suitable for the detection of antigen with two or more epitopes.

In order to be more convenient in the detection, the kit contains other detection reagents and auxiliary reagents rather than the binding molecules of the invention, such as some reagents commonly used in ELISA kits, and the characteristics and preparation methods of these reagents are known to the person skilled in the art, such as chromogenic agent, markers, secondary antibody, antibody and sensitizer. The skilled person should understand that a variety of forms of a test kit is included in the invention, as long as the binding molecule of the present invention is used for recognizing HCV.

In addition, an instruction is contained in the kit to describe the use of the reagents.

After obtained the binding molecules and/or kit of the present invention, a variety of immunological methods can be used to detect E2 protein or its content of the sample, so that the tested sample can be ensured if it is infected with HCV, and these methods are included in the present invention. Preferably, the method is for the purpose of non-disease diagnosis As a preferred method, the present invention provides an in-vitro method (non-diagnostic or therapeutic) for the detection of hepatitis C virus, including the following steps:
(a1) the tested samples are coated on the solid phase;
(a2) adding the binding molecules of the present invention into the solid phase described in (a1), so that the HCV of the tested samples can bind to the binding molecules, which forming a solid phase of binary complex with "HCV-binding molecules";
(a3) adding the tested samples of binding molecules in the present invention into the solid phase described in (a2), so that forming a solid phase of ternary complex with "HCV-binding molecules"; the tested samples contains a marker;
(a4) the marker of the ternary complex is detected, to ensure the existence or the existing amount of HCV in the tested samples.

Based on the method above, as long as set an antigen reference with the known concentration, a standard curve of the concentration is produced and the content of HCV in the tested sample can be measured by comparing the concentration in the standard curve.

The advantages of the invention are:
1) A new binding molecule is provides, which is fully human, and with induced immunogenicity and better affinity comparing to animal derived (such as murine) anti-HCV molecules. It has a better therapeutic effect and less side effect.
2) The binding molecules of the present invention can bind to the HCV E2 subunit with a native conformation, and prevent HCV from infecting susceptible host cells.

The present invention is explained with the specific examples below. These embodiments are to be understood only to illustrate the present invention and not to limit the scope of the present invention. The following examples are indicated the experimental methods of the specific conditions, usually in accordance with the conventional conditions such as the conditions set forth in J. Sam brook, eds., molecular cloning: a laboratory manual, Third Edition, Science Press, 2002, or the conditions recommended by manufacturer.

I. MATERIALS AND METHODS

The present invention is a human monoclonal antibody which neutralize HCV infection. The results can be divided into two parts:
(1) Single cell RT-PCR method to obtain the antibody gene and antibody expression;
(2) Analyze antibody characteristics.
The steps are as follow:
1. Acquisition of Peripheral Blood Mononuclear Cells (PBMC).

Peripheral blood was collected from the volunteers who have already infected with HCV, and the routine Ficoll-Paque (manufactured by Lympholyte®-H CEDARLANE) density gradient centrifugation is used to obtain more than $10^7$ of peripheral blood mononuclear cells (PBMC).

Ficoll separation method:
(1) Collecting blood in a 50 ml centrifuge tube (containing 1 ml of 4% sodium citrate), totally 10 ml of whole blood, and reversely mixed for 8-10 times. (The final concentration of sodium citrate is 0.4%);
(2) Adding some volume of RPMI1640 (containing sodium citrate), mix well;
(3) Spreading 3 ml of lymphocyte separation liquid in 15 ml transparent centrifuge tube, and carefully adding 6 ml of blood sample above it, which form a separate interface (or adding 4 ml of separation liquid with 8 ml of blood sample);
(4) Centrifuging at room temperature at 800 g for 20 min (2000 rpm, 20 min);
(5) Carefully absorbing the interface layer cells, and transfer to the new tube;
(6) Adding RPMI1640 (containing sodium citrate) to dilute for reducing liquid density. Centrifuge at 800 g/2000 rpm, for 10 min, and remove the supernatant.
(7) Washing cells with RPMI1640 for 2-3 times, for backup.

2. Sorting E2 Protein Specific Memory B Cells

FITC-CD19/APC-IgG/Cy3-HCV-E2 were used as a marker, the specific B cells were obtained into 96-well plate by FACS, and one cell per well, which obtaining E2 protein specific memory B cells.

1) Hepatitis C virus envelope protein E2 (HCV-E2) were expressed from the mammalian cell CHO expression system based on TM MAX CHO Expression System manual;
2) E2 protein was labeled by biotin: No-Weigh Sulfo-NHS-LC-Biotin (purchased from PIERCE, refers to PIERCE EZ-link Sulfo-NHS-LC-Biotin biotin labeling protocol) 10 mm reagent; the other two markers FITC-CD19 and APC-IgG were from BD bioscience
3) Labeling of sorted cells: PBMCs were divided into experiment group and control group. Markers were added according to the cell number to label the cells and staining at photophobic condition, and then the cells were filtered with 40 μm BD falcon after re-suspension with PBS.
4) Specific B cell sorting: screening with BD FACS ARIA II to get lymphocytes from PBMC based on forward and lateral angles, then obtained specific memory B cell of HCV E2 protein by compensation regulation of different control groups, which sorting into 96-well plate to carry out RT-PCR (reverse transcription PCR), one cell pre well, and placed on dry ice.

3. Antibody Gene Cloning

According to the method of Journal of Immunological Methods 329 (2008) 112-124, the antibody gene was obtained.

Obtained antibody gene was connected to pGEMT vector (purchased from Invitrogen), sequencing (BGI company), and verified antibody gene by conventional method. Heavy chain and light chain were connected to the expressing vector AbVec-hIgG and AbVec-hIgKappa respectively (Kenneth Smith et al. Rapid generation of fully human monoclonal antibodies specific to a vaccinating antigen. Nat Protoc. 2009; 4(3): 372-384).

4. Antibody Expression

The expression vector inserted with heavy chain and light chain was transient transfection with 293T cells by liposome method, and expressed humanized antibody (refers to Lipofectamine 2000 inversion manual).

(1) $1.0 \times 10^6$ cells were inoculated into 6-well plate one day before transfection.

(2) Tube A: 500 µl Opti-MEM+4 µg IgGH+4 µg IgGL (3) Tube B: 500 µl Opti-MEM+20 µl Lipofectamine Reagent;

(4) Mix tube A and tube B after 5 min, and keep at room temperature for 20 min;

(5) Mixture of tube A and tube B was added into cell culture plate, incubated at 37° C. for 6 h;

(6) Adsorbing culture medium containing Lipofectamine Reagent DNA after 6 h, 2 ml FreeStyle™ 293 Expression Medium was added into each well;

(7) Collecting cell supernatant after 72 h, at 4° C., 3000 rpm, 5 min.

5. Antigen Specificity Assay

Detecting the expression of the humanized antibody if the antibody can recognize HCV-E2 (expressed by mammalian cell CHO system; refers to FreeStyle MAX CHO Expression System manual), and detect the binding ability to antigen.

(1) Coating HCV-E2 on the ELISA plate (purchased from NUNC), 10 m/ml, two replicates per sample, 100 µl per well, overnight at 4° C.

(2) Washing plate with PBST for three times;

(3) Blocking: 1% BSA, 200 µl per well, at 37° C., for 2 h;

(4) Washing plate with PBST for three times;

(5) According to the determination of concentration, adjust the humanized antibody cell supernatant to the same concentration, 100 µl per well, HCV patients' plasma was set as positive control, at 37° C., for 2 h;

(6) Washing plate with PBST for three times;

(7) Goat Anti-Human IgG (Fc specific)—Peroxidase antibody, 1:10000 dilution, 100 µl per well, added into sample and positive control ELISA plate, at 37° C., for 1 h;

(8) Washing plate with PBST for three times;

(9) Substrate A:B=1:1, substrate is TMB, 3, 3', 5, 5'-tetramethyl benzidine (purchased from Sigma, use as manual). 100 µl per well, at 37° C., for 15 min, react at photophobic condition;

(10) 50 µl of 2M $H_2SO_4$ was added;

(11) The absorbance (OD450) at the wavelength of 450 nm was determined by spectrophotometer, and the data were processed.

6. Neutralizing Activity Test of Antibody—Euvirus Neutralizing Experiment

1) Digesting huh7.5.1 cells, re-suspension with DMEM containing 10% serum, spread on the 96-well plate at the density of $10^5$/ml, culture for 12-24 h 2) Diluting virus to $1-2 \times 10^3$ ffu/ml (focus-forming units per milliliter of supernatant) with DMEM containing 10% serum, and adding appropriate amount of antibody, incubating at 37° C., for 1 h, 3) Aspirating huh7.5.1 culture fluid from 96-well plate, and add 100 ul of incubated virus. Replacing fresh DMEM containing 10% serum after 24 h, and incubate for 48 h, 4) Fixing cells with 100 ul of PFA, keep for 30 min at room temperature, 5) Adding PBS containing 0.3% TritonX-100, 3% BSA, 10% FBS, incubate for 1 h at room temperature, 6) Adding anti-NS3 (or NS5A, or core) primary antibody, incubate for 1.5 h at room temperature, 7) Washing with PBS for 3 times, 5 min for each, 8) Adding anti-mouse secondary antibody containing fluorescence, incubate for 1 h at room temperature, 9) Washing with PBS for 3 times, 5 min for each, 10) Recording the number of virus infected cell in each well with fluorescence microscope.

II. EXAMPLES

Example 1. HCV-E2 Protein Specific Memory B Cells

Specific B cells were isolated by using FITC-CD19/APC-IgG/Cy3-HCV-E2 as a specific marker, as shown in FIG. 1.

Example 2. Antibody Gene

Figure 2:
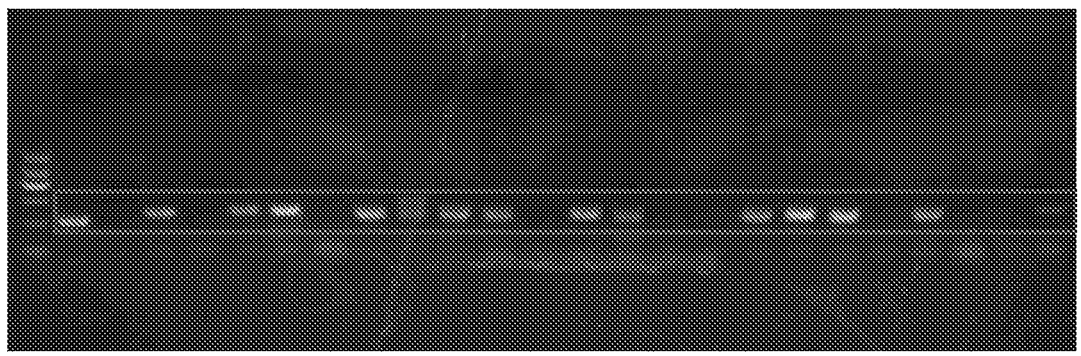
FIG. 2 Electrophoresis results of PCR amplification product in which β-actin is used as the internal standard FIG. 3 Electrophoresis results of PCR amplification products of heavy chain gene FIG. 4 Electrophoresis results of PCR amplification products of light chain gene FIG. 5. Specific antigen detection for human monoclonal antibodies (including 8D6).
Figure 3:
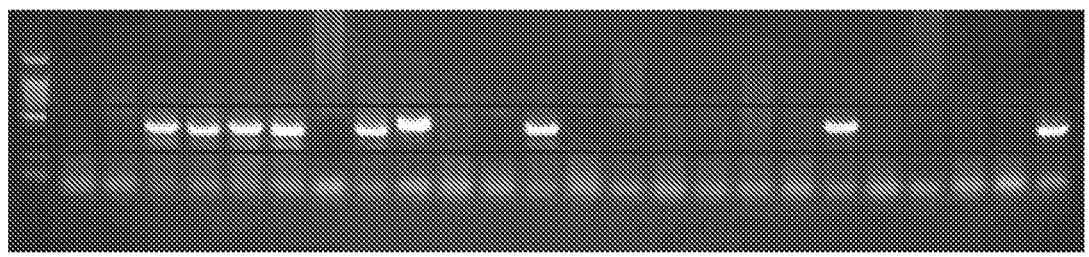
Figure 4:
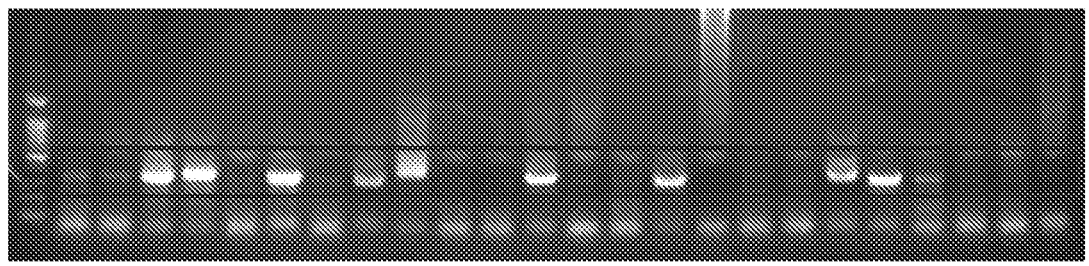

Antibody heavy and light chain variable region gene was obtained by RT-PCR and Nested-PCR, molecular weight was about 400 bp, and β-actin was the internal control (343 bp), electrophoresis is shown in FIG. 2, FIG. 3, and FIG. 4. Heavy chain and light chain variable region gene derived from the same B cells were connected with T vector, sequenced and constructed the expression vector.

8D6 heavy chain variable region gene sequences are as follows (SEQ ID NO: 1):

GAGGTGCAGCTGGTGCAGTCTGGGTCTGAGTTGAAGAAGCCTGGGGCCTC

ACTGAAGCTCTCCTGCAAGGCTTCTGGATACACCTACATTACCCCTGCCA

TGAAC(CDR1) TGGGTGCGACAGGCCCCTGGACATGGGCTTGAGTGGATG

GGAGGAATCAACACCAACACTGGGAACCCAACCTATGCCCAGGGCTTCGC

AGGA(CDR2) CGGTTTGTCTTCTCCTGGGACACCTCTGTCAGCACGGCAT

ATCTGCATATCAGCAGCCTAAAGACTGAGGACACTGCCGTCTATTACTGT

GCGGACACCCGAATCTTTTCTTGTCGGCGTGGAACGTGCTATGGTGGTTT

CGATGTC(CDR3) TGGGGCCAAGGGACAATGGTCACCGTCTCTTCAG

Note:
the underlined parts are the high variable regions in the heavy chain gene variable region, which are CDR1 (SEQ ID NO: 5), CDR2 (SEQ ID NO: 6), CDR3 (SEQ ID NO: 7).

8D6 heavy chain variable region amino acid sequences are as follows (SEQ ID NO: 2):

EVQLVQSGSELKKPGASLKLSCKASGYTYITPAMN(CDR1)WVRQAPGHG
LEWMGGINTNTGNPTYAQGFAG(CDR2)RFVFSWDTSVSTAYLHISSLKT
EDTAVYYCADTRIFSCRRGTCYGGFDV(CDR3)WGQGTMVTVSS
Note:
the underlined parts are heavy chain amino acid sequence CDR1 (SEQ ID NO: 8), CDR2 (SEQ ID NO: 9), CDR3 (SEQ ID NO: 10).

8D6 light chain variable region gene sequences are as follows (SEQ ID NO: 3):

```
GACATCCAGATGACCCAGTCTCCATCCTCCCTGTCTGCATCTGTAGGAG

ACAGAATCACCATCACTTGCCGGGCAAGTCAGAGCATTAGCAACTTTTA

AAT(CDR1)TGGTTTCAGCATAGACCGGGGAAAGCCCCTAAACTCCTGAT

CTATGGTGCAACCATTTTGCAAAGT(CDR2)GGGGTCCCATCAAGGTTCA

GTGGCAGTGGATCTGGGACAGATTTCACTCTCACCATCAGCAGTCTGCAA

CCTGAAGATTTTGCAACTTACTACTGTCAACAGAGTGACAGTAGTACCTA

CATC(CDR3)TTTGGCCAGGGGACCAAGGTGGAAATCAAAC
```
Note:
the underlined parts are the high variable regions in the light chain gene variable region, which are CDR1 (SEQ ID NO: 11), CDR2 (SEQ ID NO: 12), CDR3 (SEQ ID NO: 13).

8D6 light chain variable region amino acid sequences are as follows (SEQ ID NO: 4):

```
DIQMTQSPSSLSASVGDRITITCRASQSISNFLN(CDR1)WFQHRPGKAP
KLLIYGATILQS(CDR2)GVPSRFSGSGSGTDFTLTISSLQPEDFATYYC
QQSDSSTYI(CDR3)FGQGTKVEIK
```
Note:
the underlined parts are light chain amino acid sequences CDR1 (SEQ ID NO: 14), CDR2 (SEQ ID NO: 15), CDR3 (SEQ ID NO: 16).

Example 3. Antigen Specificity of Antibody

ELISA results showed that 8D6 humanized antibody has specific binding capacity for CHO expressed HCV-E2.

Figure 5:
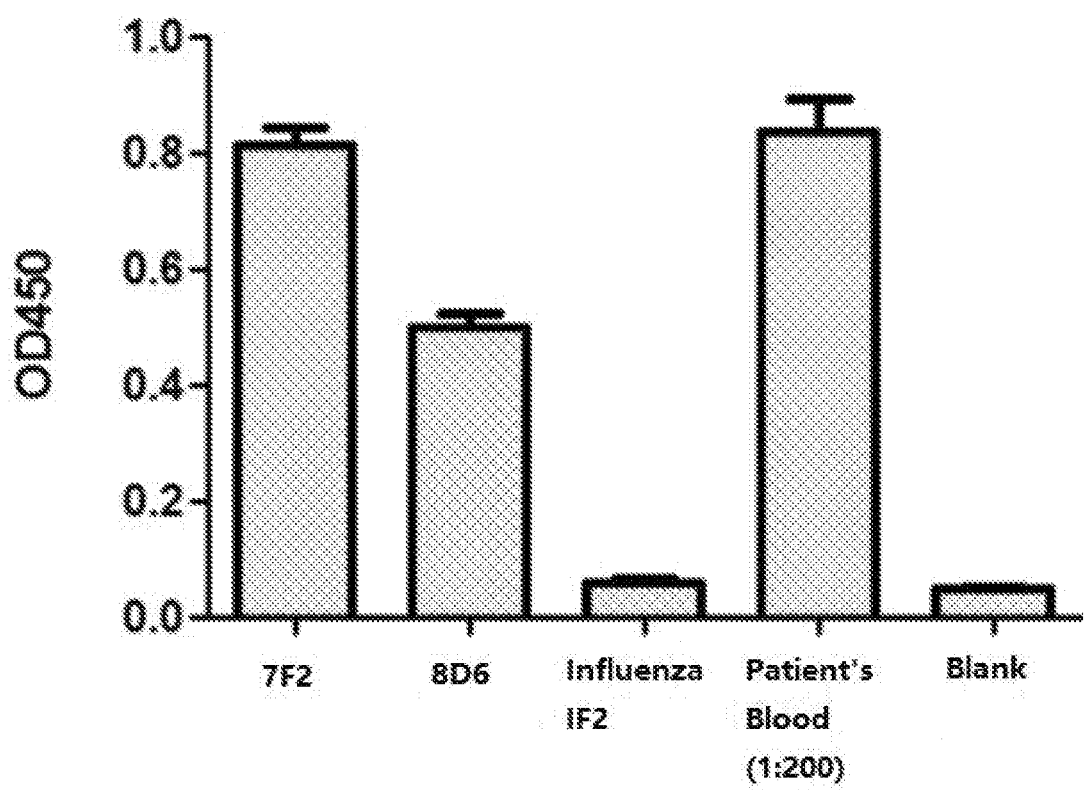

As shown in FIG. 5, this experiment, using HCV infected patients' plasma as a positive control, and using a cell culture and an influenza virus antibody 1F2 (refers to Fully human broadly neutralizing monoclonal antibodies against influenza A viruses generated from the memory B cells of a 2009 pandemic H1N1 influenza vaccine recipient. Hu W, Chen A, Miao Y, Xia S, Ling Z, Xu K, et al. Virology. 2013 Jan. 20; 435(2): 320-8. doi: 10.1016/j.virol.2012.09.034.) as a negative control.

Example 4. Neutralizing Activity of Antibody

Humanized monoclonal antibody (8D6) is expressed with 293T, adjust the concentration to 50 µg/ml, 10 µg/ml, 2 µg/ml, 0.4 µg/ml and 0.08 µg/ml after purification for euvirus neutralizing experiment which determine the neutralizing activity, which is the inhibit rate of HCV euvirus. The euvirus used for experiment contain PR52B6M, PR79, JFH1 (international standard strain), PR26C3M, D183(2a) (international standard strain), and all the strains set forth above was from Chinese Academy of Science, Institute Pasteur of Shanghai.

Figure 6:
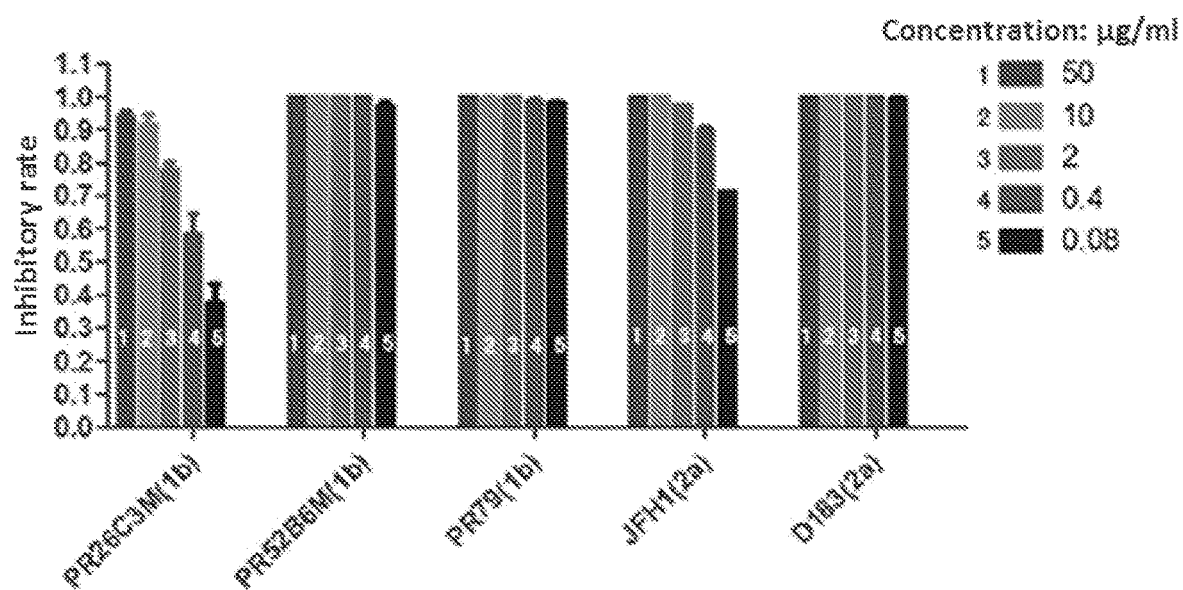
FIG. 6. The neutralizing activity of the human monoclonal antibody (8D6) for the HCV euvirus (1b subtype PR26C3M, PR52B6M, PR79 three strains; 2A subtype PR79, JFH1 strain)
Figure 7:
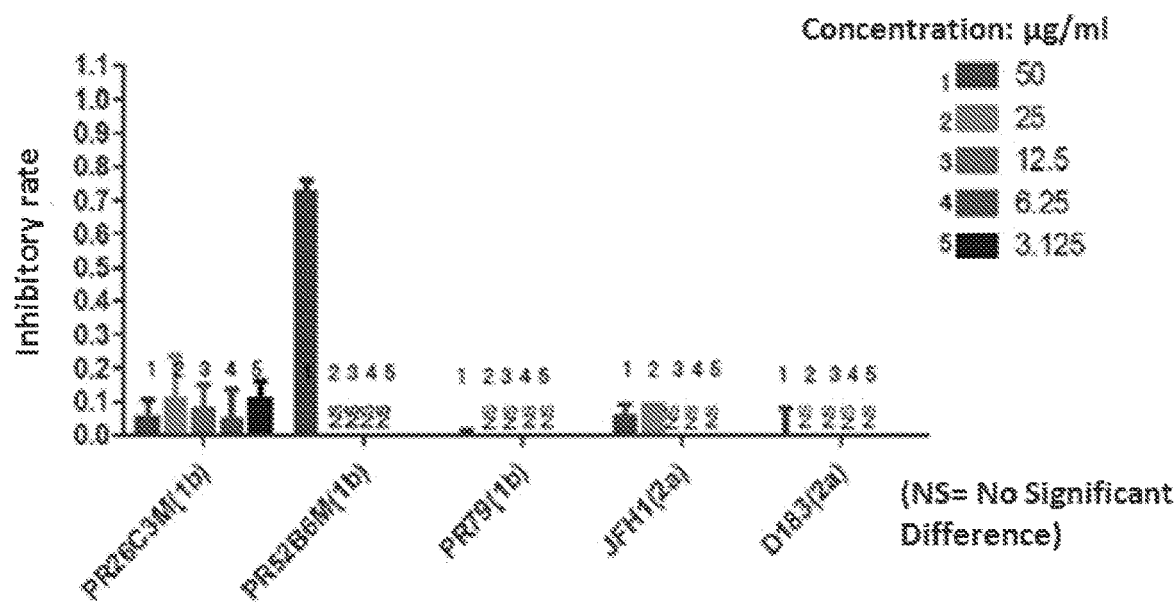
FIG. 7. The detection of neutralizing activity for anti-HCV E2 1F2 against HCV euvirus.

As shown in FIG. 6-7, compared to negative control (human mAbs 1F2 of a strain of influenza virus HA protein), experimental group (humanized monoclonal antibody 8D6 for anti-HCV E2 protein) has more than 90% of inhibition rate for 1b subtype in PR52B6M, PR79 two strains and 2a subtype D183, JFH1 two strains of HCV euvirus, when the concentration is higher than 0.4 µg/ml, and it has more than 90% inhibition rate for another strain 1b subtype PR26C3M when the concentration is 10 µg/ml.

Example 5. The Binding Activity of 8D6 to the Surface Glycoprotein E2 of HCV Strains with Different Genotypes was Verified by ELISA Glycoprotein E2 of different HCV genotypes was expressed in 293T cells (Table 1, and C-terminal with 6×HIS tag), and collect cell supernatant, then added the prepackaged 8D6 antibody to 96-microwell plates, incubate at 37° C. for 2 hours, after washing away impure proteins, detect with a monoclonal antibody of mouse-anti HIS tag. The absorbance (OD450) at the wavelength of 450 nm was determined by spectrophotometer, and the data were processed.

TABLE 1

GenBank No. of glycoprotein E2 of different HCV genotypes

| Virus strain (genotype) | Glycoprotein E2 GenBank No. |
| --- | --- |
| H77(1a) | JF343780.2 |
| Con1(1b) | AJ238799.1 |
| HCR6(1b) | AY045702.1 |
| PR52(1b) | HQ912958.1 |
| PR26(1b) | HQ912956.1 |
| PR79(1b) | HQ912959.1 |
| JFH1(2a) | AB047639.1 |
| J8(2b) | JF343783.1 |
| Patient 28(3a) | GQ356213.1 |
| ED43(4a) | JF343785.1 |
| SA13(5a) | JF343786.1 |
| HK6a(6a) | JF343787.1 |
| 74(6a) | DQ480524.1 |
| QC69(7a) | FJ230884.1 |

Figure 8:
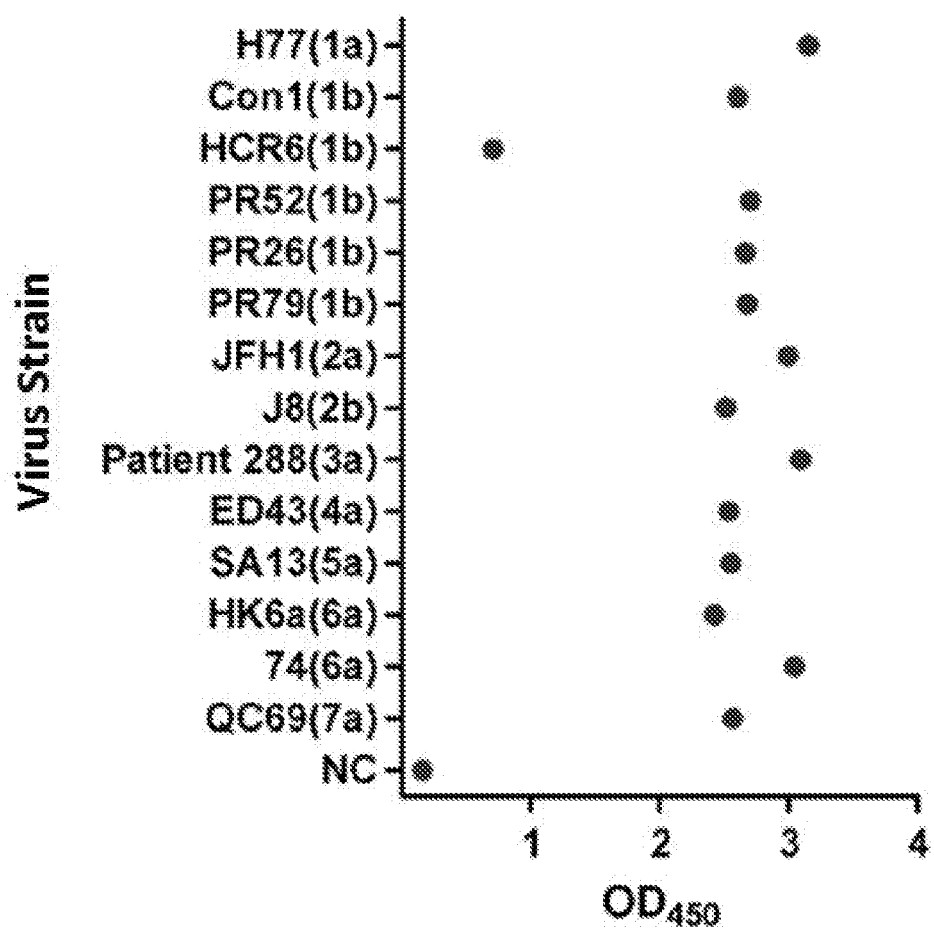
FIG. 8. The binding activity of 8D6 on the surface glycoprotein E2 of HCV strains with different genotypes was verified by ELISA.

Results as shown in FIG. 8, the 8D6 antibody showed a broad spectrum of binding activity for different genotypes of HCV.

Example 6. Determination of Neutralizing Activity of Antibody Against Euvirus Different subtypes of HCV (Table 2) particles and gradient diluted 8D6 antibody were incubated at room temperature for 1 hour, then added into Huh-7.5 cells for incubation, after three hours of incubation, sucked cell supernatant, and adding fresh cell culture medium, additional incubate for 72 hours. The expression level of NS5A was detected by determining the number of cell colonies with fluorescence after HCV infected cells was fixed by 4% paraformaldehyde, and then the cells were infected by HCV. The IC50 of the antibody is the concentration of the antibody which is inhibited by 50% when the virus is infected, which was analyzed by statistical software.

TABLE 2

Information on different HCV strains

| Subtype | Virus | GenBank No. |
| --- | --- | --- |
| 1a | H77 | JF343780.2 |
| 1b | Con1 | AJ238799.1 |
| 1b | PR26 | HQ912956.1 |
| 1b | PR52 | HQ912958.1 |
| 1b | PR79 | HQ912959.1 |
| 2a | JFH7 | AB047639.1 |
| 2a | PR63 | KF676351 |
| 2b | J8 | JF343783.1 |
| 3a | S52 | JF343784.2 |
| 4a | ED43 | JF343785.2 |
| 5a | SA13 | JF343786.2 |

TABLE 2-continued

Information on different HCV strains

| Subtype | Virus | GenBank No. |
|---|---|---|
| 6a | HK6a | JF343787.2 |
| 7a | QC69 | FJ230884.1 |

IC50 of 8D6 antibody was shown in Table 3.

TABLE 3

The micro neutralization activity of 8D6 was verified by the HCV euvirus system of cell culture.

| Virus strain | Subtype | 8D6 IC50 (µg/ml) |
|---|---|---|
| PR52 | 1b | <0.08 |
| PR26 | 1b | 0.412 |
| Con1 | 1b | 2.426 |
| PR79 | 1b | <0.08 |
| JFH1 | 2a | 0.003 |
| PR63 | 2a | <0.016 |
| D183 | 2a | <0.08 |
| J8 | 2b | 10 |
| S52 | 3a | 0.01 |
| SA13 | 5a | 0.087 |
| HK6a | 6a | 0.0015 |

As shown in Table 3, 8D6 has a good micro neutralizing activity at a lower concentration, and the neutralizing activity is broad spectrum.

All the literatures referred in this invention are as the reference, as each literature is cited as a reference. In addition to be understood, after reading all the content of the invention, the technicians in this field can make a variety of changes or modifications to the invention, and these equivalent forms also contains in the rights attached to claim defined scope.

The invention claimed is:

1. An isolated binding molecule, wherein the binding molecule comprises CDR1 heavy chain set forth in SEQ ID NO: 8, CDR2 heavy chain set forth in SEQ ID NO: 9, CDR3 heavy chain set forth in SEQ ID NO: 10, CDR1 light chain set forth in SEQ ID NO: 14, CDR2 light chain set forth in SEQ ID NO: 15, and CDR3 light chain set forth in SEQ ID NO: 16; wherein said isolated binding molecule is an antibody; and wherein said binding molecule specifically binds to hepatitis C virus E2 protein.

2. The binding molecule according to claim 1, wherein the binding molecule comprises heavy chain variable region which contains amino acid sequence set forth in SEQ ID NO: 2.

3. The binding molecule according to claim 1, wherein the binding molecule comprises light chain variable region which contains amino acid sequence set forth in SEQ ID NO: 4.

4. The binding molecule according to claim 1, wherein the binding molecule comprises heavy chain variable region and light chain variable region, which contain amino acid sequences set forth in SEQ ID NO: 2 and SEQ ID NO: 4 respectively.

5. The binding molecule according to claim 1, wherein the binding molecule is a whole immunoglobulin molecule, a monoclonal antibody, single chain antibody (scFv), bivalent single-chain antibody, single strand phage antibody, double specific double-chain antibody, three-chain antibodies, four-chain antibody, chimeric antibody, or Fab, F(ab'), F(ab')$_2$, Fv, dAb, Fd fragment.

6. The binding molecule according to claim 1, wherein the binding molecule comprises IgH sequence and Igκ sequence.

7. A nucleic acid molecule coding the binding molecule according to claim 1.

8. An expression vector, comprising a DNA coding the binding molecule according to claim 1.

9. A host cell, wherein the host cell comprises the expression vector of claim 8.

10. A composition, comprising the binding molecule according to claim 1, and pharmaceutical acceptable carrier.

11. A kit for detecting HCV, comprising the binding molecule according to claim 1.

12. A method for inhibiting HCV comprising administering the binding molecule of claim 1 to a patient infected with HCV.

13. A method for detecting HCV, comprising the steps of contacting the binding molecule according to claim 1 with a sample, and, confirming the existence of HCV and detecting the existing amount of HCV by testing the binding status of the binding molecule and the sample.

14. The kit of claim 11, wherein the HCV is 1a subtype, 1b subtype, 2a subtype, 2b subtype, 3a subtype, 4a subtype, 5a subtype, 6a subtype or 7a subtype virus.

15. The kit of claim 14, wherein
the HCV 1a subtype comprises H77 strain; or
the HCV 1b subtype comprises PR52B6M strain, PR79 strain, PR26C3M strain, Con1 strain, HCR6 strain, PR52 strain, PR26 strain, PR79 strain; or
the HCV 2a subtype comprises D183 strain, JFH1 strain, PR63 strain; or
the HCV 2b subtype comprises J8 strain; or
the HCV 3a subtype comprises Patient 288 strain, S52 strain; or
the HCV 4a subtype comprises ED43 strain; or
the HCV 5a subtype comprises SA13 strain; or
the HCV 6a subtype comprises HK6a strain, 74 strain; or
the HCV 7a subtype comprises QC69 strain.

* * * * *